United States Patent
Bax et al.

(10) Patent No.: US 10,816,132 B2
(45) Date of Patent: Oct. 27, 2020

(54) COUNTERBALANCING MECHANISM AND STABILIZER DESIGN AND METHOD FOR COUNTERBALANCING AND STABILIZING A LOAD

(71) Applicant: Aaron Fenster, London (CA)

(72) Inventors: Jeffrey Bax, Lucan (CA); Aaron Fenster, London (CA)

(73) Assignee: Aaron Fenster, London (CA)

( * ) Notice: Subject to any disclaimer, the term of this patent is extended or adjusted under 35 U.S.C. 154(b) by 0 days.

(21) Appl. No.: 16/124,409

(22) Filed: Sep. 7, 2018

(65) Prior Publication Data

US 2019/0076115 A1 Mar. 14, 2019

Related U.S. Application Data

(60) Provisional application No. 62/556,074, filed on Sep. 8, 2017.

(51) Int. Cl.
*F16M 13/02* (2006.01)
*F16M 11/10* (2006.01)
(Continued)

(52) U.S. Cl.
CPC ......... *F16M 11/14* (2013.01); *F16M 11/2014* (2013.01); *F16M 11/2078* (2013.01); *F16M 11/24* (2013.01); *F16M 13/02* (2013.01); *A61B 8/4218* (2013.01); *A61B 8/4245* (2013.01); *A61B 8/4461* (2013.01); *F16M 11/08* (2013.01);
(Continued)

(58) Field of Classification Search
CPC ....... F16M 2220/063; F16M 2220/041; F16M 2220/044; F16M 13/04; F16M 11/10; B25J 19/0016
See application file for complete search history.

(56) References Cited

U.S. PATENT DOCUMENTS 4,447,031 A * 5/1984 Souder, Jr. ............ F16M 11/126
248/281.11
6,206,832 B1 3/2001 Downey et al.
(Continued)

OTHER PUBLICATIONS

Sharon Joines, Tamara James, and Gisela Suarez. "Upper Extremity Pain in." Advances in Human Factors and Ergonomics in Healthcare (2010): 114.
(Continued)

*Primary Examiner* — Patrick Cicchino
(74) *Attorney, Agent, or Firm* — John Maldjian; Maldjian Law Group LLC

(57) ABSTRACT

The present invention relates to a resilient member aided counterbalancing and stabilizing device and method for resilient member aided counterbalancing and stabilizing loads in the direction of gravity. The device preferably includes a quick release mechanism in each design and a counterbalance assembly which in preferred embodiments is used to aid in the precise positioning of a stabilizer which in turn supports a load (e.g., a medical device). The quick release assembly in each stabilizer design preferably includes a central housing containing at least one ball joint(s) which is preferably connected to the counterbalancing linkage that supports the load. To unlock the mechanism, the user preferably squeezes a trigger mechanism which directly loosens the locks responsible for holding the load in place.

7 Claims, 14 Drawing Sheets

(51) Int. Cl.
*F16M 11/14* (2006.01)
*F16M 11/20* (2006.01)
*F16M 11/24* (2006.01)
*G01N 29/265* (2006.01)
*A61B 8/00* (2006.01)
*F16M 11/08* (2006.01)
*F16M 11/22* (2006.01)
*G01N 29/22* (2006.01)

(52) U.S. Cl.
CPC .......... *F16M 11/10* (2013.01); *F16M 11/2092* (2013.01); *F16M 11/22* (2013.01); *F16M 2200/022* (2013.01); *F16M 2200/044* (2013.01); *F16M 2200/047* (2013.01); *F16M 2200/048* (2013.01); *F16M 2200/063* (2013.01); *G01N 29/225* (2013.01); *G01N 29/265* (2013.01)

(56) References Cited

U.S. PATENT DOCUMENTS

| | | | |
|---|---|---|---|
| 7,562,851 B2 * | 7/2009 | Hein | ............... F16M 11/2014 248/276.1 |
| 8,444,543 B2 | 5/2013 | Fenster et al. | |
| 8,788,019 B2 | 7/2014 | Downey et al. | |
| 8,899,125 B2 | 12/2014 | Bax et al. | |
| 10,052,083 B2 | 8/2018 | Barker et al. | |
| 10,066,782 B2 | 9/2018 | Bax et al. | |
| 2008/0004481 A1 | 1/2008 | Bax et al. | |
| 2009/0234369 A1 | 9/2009 | Bax et al. | |
| 2014/0121675 A1 | 5/2014 | Bax et al. | |
| 2014/0135790 A1 | 5/2014 | Fenster et al. | |
| 2016/0346940 A1 * | 12/2016 | Bax | ....................... A61B 90/11 |
| 2018/0051850 A1 | 2/2018 | Bax et al. | |
| 2018/0058529 A1 | 3/2018 | Bax et al. | |
| 2018/0112817 A1 | 4/2018 | Bax et al. | |
| 2018/0161114 A1 | 6/2018 | Bax et al. | |

OTHER PUBLICATIONS

Beth W. Orenstein "Scanning in Pain—Sonographers Seek Relief From Job-Related Hazard" Radiology Today (2009): vol. 10 No. 18 p. 24.

* cited by examiner

COUNTERBALANCING MECHANISM AND STABILIZER DESIGN AND METHOD FOR COUNTERBALANCING AND STABILIZING A LOAD

CROSS-REFERENCE TO RELATED APPLICATIONS

This application claims the benefit of U.S. provisional patent application Ser. No. 62/556,074 filed Sep. 8, 2017, the entire contents of which is herein incorporated by reference.

FIELD

The present invention relates generally to a counterbalancing mechanism and stabilizer design and more particularly to a resilient member aided counterbalancing mechanism and stabilizer design.

BACKGROUND

Most medical devices require a support apparatus (or stabilizer) to coarsely position a medical device with a high degree of flexibility and with little effort by the health care worker. Once in a desired position, the stabilizer is preferably locked to allow for further fine adjustment of the position of a given medical device if necessary. Stabilizer mechanisms of the prior art have been difficult to manipulate by a user (e.g., a physician) and have been unreliable where the stabilizer is cumbersome due to the lack of a payload support and the locking mechanism becoming seized making it difficult for the user to use the device.

Many scientific, medical and industrial tasks involve the deployment of objects or instruments, which need to be held aloft and manipulated in space for extended periods of time, which may result in repetitive stress to a user. The resulting repetitive stresses are known to be a cause of work-related trauma. For example, work related musculoskeletal disorders have been identified as a widespread problem amongst diagnostic medical sonographers and vascular technologists. [2] In 2006, approximately 46,000 sonographer and vascular technologist job positions existed in the United States. [2] A representative survey reported nearly 90% of sonographers and vascular technologists report completing ultrasound scans while in some sort of pain. [3] Aggravating factors for pain during procedures was reported by sonographers to include sustained and repeated twisting of the neck and body, sustained arm abduction and application of pressure on the ultrasound transducer.

In a further example, heavy tools or parts may require maneuvering in repetitive or awkward motions by workers in industrial settings. Workers may also be required to maintain fixed poses for extended periods of time. Poor ergonomics may adversely affect the productivity as well as the health and safety of workers within industrial settings.

To improve worker ergonomics, various devices may have been developed to counterbalance objects and instruments, including, but not limited to, heavy tools or parts. While fixed arm supports that permit some lateral motion are known in the art, some tasks require a larger range of horizontal and vertical motions (e.g., at least two or three degrees of freedom). Industrial, medical and scientific operations including, but not limited to surgical, diagnostic and therapeutic procedures, could greatly benefit from having the force of gravity reduced (e.g., effectively negated) for the user in a manner that provides larger ranges of motion in an isoelectric manner. The term isoelectric refers to the application of a constant force by the user to move the arm throughout its full range of motion. For example, Equipois. Inc. (Manchester, N.H.) has developed spring loaded counterbalancing arms including self-supporting counterbalancing arms adapted to position tools and parts in industrial settings employing serially connected parallelogram segments. Springs are used to counterbalance the load and any subsequent segments in the arm. The preload of the spring in each segment may be adjusted to accommodate loads of varying weights.

Such prior art devices present many drawbacks however. To adjust the load carrying capacity of the arm, the user may be required to make multiple adjustments to various elements making the use thereof slow and cumbersome. If the arm is not isoelastic, the user may experience inconsistent performance as the user may need to use greater force to adjust the arm in different positions. The isoelasticity of the zeroG (Equipois. Inc.) is inversely related to the amount of rate adjustment. As rate adjustment increases to allow operation at extreme angles, isoelasticity decreases degrading the overall performance throughout the full range of motion.

In the field of diagnostic medical sonography and vascular technology, for example, previous counterbalancing arms have used high torque motors to counterbalance the load weight creating potential harm for the patient. In the event of a malfunction, the motors potentially drive the arm into the patient with a minimum force of twice the weight of the arm. In the event of a power failure, a traditional arm may lose its pose and slump under its own weight as the motors can no longer counterbalance the weight. While brakes (or transmissions with high gear ratios) have been applied to prevent such motorized arms from slumping in a power failure, the traditional arm may become fully locked (i.e., not adjustable) until power is restored.

Prior attempts to solve the problems associated with prior art devices has led to a compromise in either the sensitivity due to the increased mass and size of the mechanism, or accuracy of the counterbalance mechanism causing increased effort of the operator to manipulate the payload.

What is needed is a device and/or method that overcomes one or more of the limitations associated with the prior art.

More particularly, what is needed is a counterbalance apparatus and/or a method that overcomes one or more of the limitations associated with the prior art.

SUMMARY

One of the objectives of an aspect of the present invention is to provide an apparatus and/or method which facilitates the counterbalancing of loads having different weights which is compact, lightweight and isoelastic throughout the range of motion of the arm.

One of the objectives of an aspect of the present invention is to provide a device and/or method for counterbalancing a load in linkage systems that lack a counterbalancing mechanism.

One of the objectives of an aspect of the present invention is to provide a simple, compact and light-weight counterbalancing mechanism compared to the prior art.

One of the objectives of an aspect of the present invention is to provide a device and/or method for sensitive and/or precise counterbalancing a load for a one arm stabilizer assembly.

One of the objectives of an aspect of the present invention is to provide a device and/or method for sensitive and/or precise counterbalancing a load for a two-arm stabilizer assembly.

It is an object of the present invention to obviate and/or mitigate one or more of the aforementioned disadvantages and/or shortcomings associated with the prior art, to provide one of the aforementioned needs, and/or to achieve one or more of the aforementioned objectives.

The present invention facilitates the sensitive and/or precise counterbalancing of loads with the aid of one or more resilient members. The device and method preferably include a quick release mechanism in each design and a counterbalance assembly which in preferred embodiments is used to aid in the precise positioning of a stabilizer which in turn supports a load (e.g., a medical device). The quick release assembly in each stabilizer design preferably includes a central housing containing at least one ball joint(s) which is preferably connected to the counterbalancing linkage that support the load. To unlock the mechanism, the user preferably squeezes the trigger mechanism which directly loosens the locks responsible for holding the load in place.

The design of the present invention is preferably simpler and more compact than any other available counterbalancing systems allowing it to be easily adapted to a linkage while adding a minimum amount of weight (and inertia) to the mechanism thus making it easier for the user to manipulate the payload. In addition, the system has the capacity to carry greater payloads than prior art designs.

According to an aspect of the invention, the device and/or method provides resilient member aided counterbalancing and stabilizing of loads to facilitate sensitive and/or precise manipulation of the various loads.

According to an aspect, there is provided a counterbalance apparatus for supporting a load having a load vector applied in a direction of the vector of gravity, comprising: a base; a load bearing arm comprising a plurality of pivot points forming one or more parallelogram linkages projecting from the base at an attachment point at a proximal end and adapted to support the load at a distal end; a first resilient member for applying a force to the load bearing arm having a first end connected to a position at the distal end of the arm and a second end connected to a first adjustment member pivotally connected to the base and positioned at a first proximal end of the arm; a second resilient member for applying a force to the load bearing arm having a first end connected to the position at the distal end of the arm and a second end connected to a second adjustment member pivotally connected to the base and positioned at a second proximal end of the arm; the first and second adjustment members moveable between a non-load bearing and a load bearing position; and wherein movement of the first and/or second adjustment members from the non-load bearing position to the load bearing position engages the forces of the first and second resilient members to counterbalance the load vector.

According to an aspect, there is provided a method of supporting a load having a load vector applied in a direction of the vector of gravity using a counterbalance apparatus, the method comprising: attaching the load to a distal end of a load bearing arm projecting from a base at an attachment point at a proximal end, the load bearing arm with a plurality of pivot points forming one or more parallelogram linkages; configuring a first resilient member to apply a force to the load bearing arm by connecting a first end to a position at the distal end of the arm and a second end to a first adjustment member pivotally connected to the base and positioned at a first proximal end of the arm; configuring a second resilient member to apply a force to the load bearing arm by connecting a first end to the position at the distal end of the arm and a second end to a second adjustment member pivotally connected to the base and positioned at a second proximal end of the arm; adjusting the first and second adjustment members between a non-load bearing and a load bearing position; and whereby moving the first and/or second adjustment members from the non-load bearing position to the load bearing position engages the forces of the first and second resilient members to counterbalance the load vector.

According to an aspect, there is provided a locking mechanism for use with the apparatus, the locking mechanism comprising: a toggle linkage slidably connected to a locking shaft, the locking shaft extending through an opening in a main body of the locking mechanism to a split ball joint, wherein a first end of the locking shaft is rigidly connected to an upper portion of the split ball joint and a second end of the locking shaft is rigidly connected to a trigger mechanism; an upper lever adapted to engage the toggle linkage; a lower lever adapted to disengage the toggle linkage; wherein movement of the upper lever from a disengaged position to the engaged position moves the toggle linkage into a locked position by separating the split ball joint; and wherein movement of the lower lever from the engaged position to the disengaged position moves the toggle linkage into an unlocked position by rejoining the split ball joint.

Further features will be described or will become apparent in the course of the following detailed description. It should be understood that each feature described herein may be utilized in any combination with any one or more of the other described features, and that each feature does not necessarily rely on the presence of another feature except where evident to one of skill in the art.

DETAILED DESCRIPTION OF THE DRAWINGS

For clearer understanding, preferred embodiments will now be described in detail by way of example, with reference to the accompanying drawings, in which.

Figure 1A:
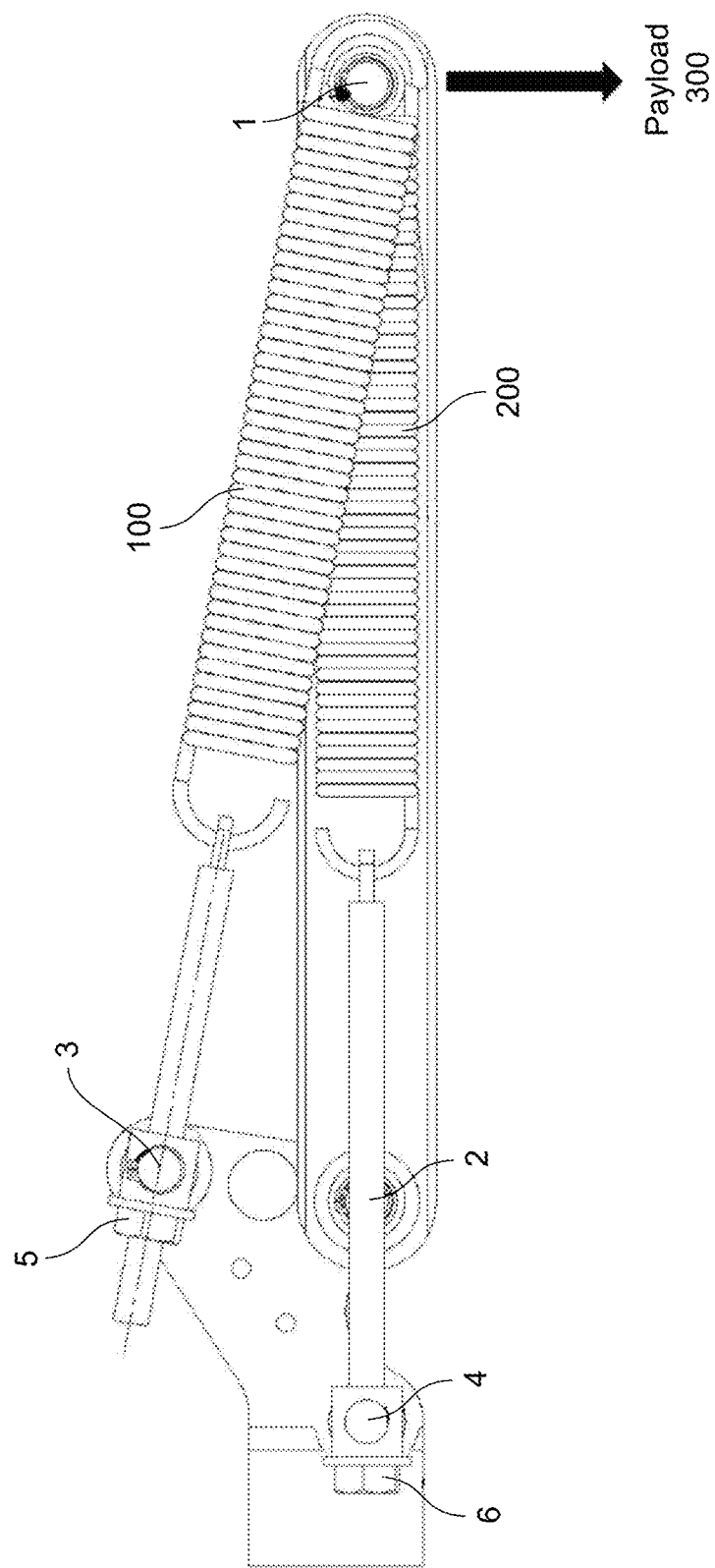
FIG. 1A depicts a first embodiment of a counterbalance apparatus integrated to support a payload attached to a hinged lever.
Figure 2A:
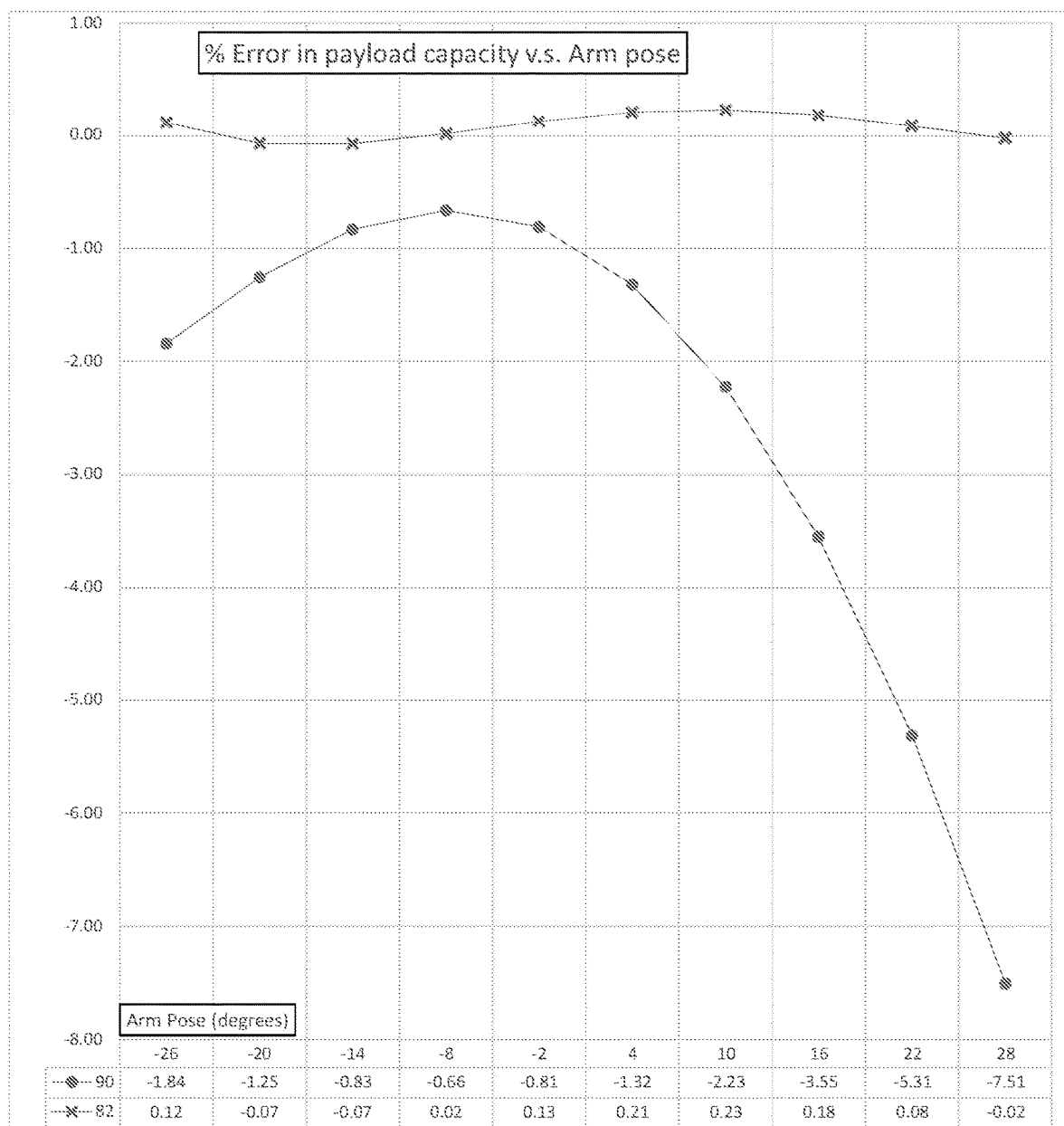
FIG. 2A depicts a graph showing the percentage error in payload carrying capacity of an arm vs. arm pose relative to the horizontal in degrees for a resilient member balance design that uses two commercial extension springs in the design described by Bax et al. [1] in thin dotted line (lower line) compared to an improved design geometry of the present invention (thick solid line or upper line)
Figure 2B:
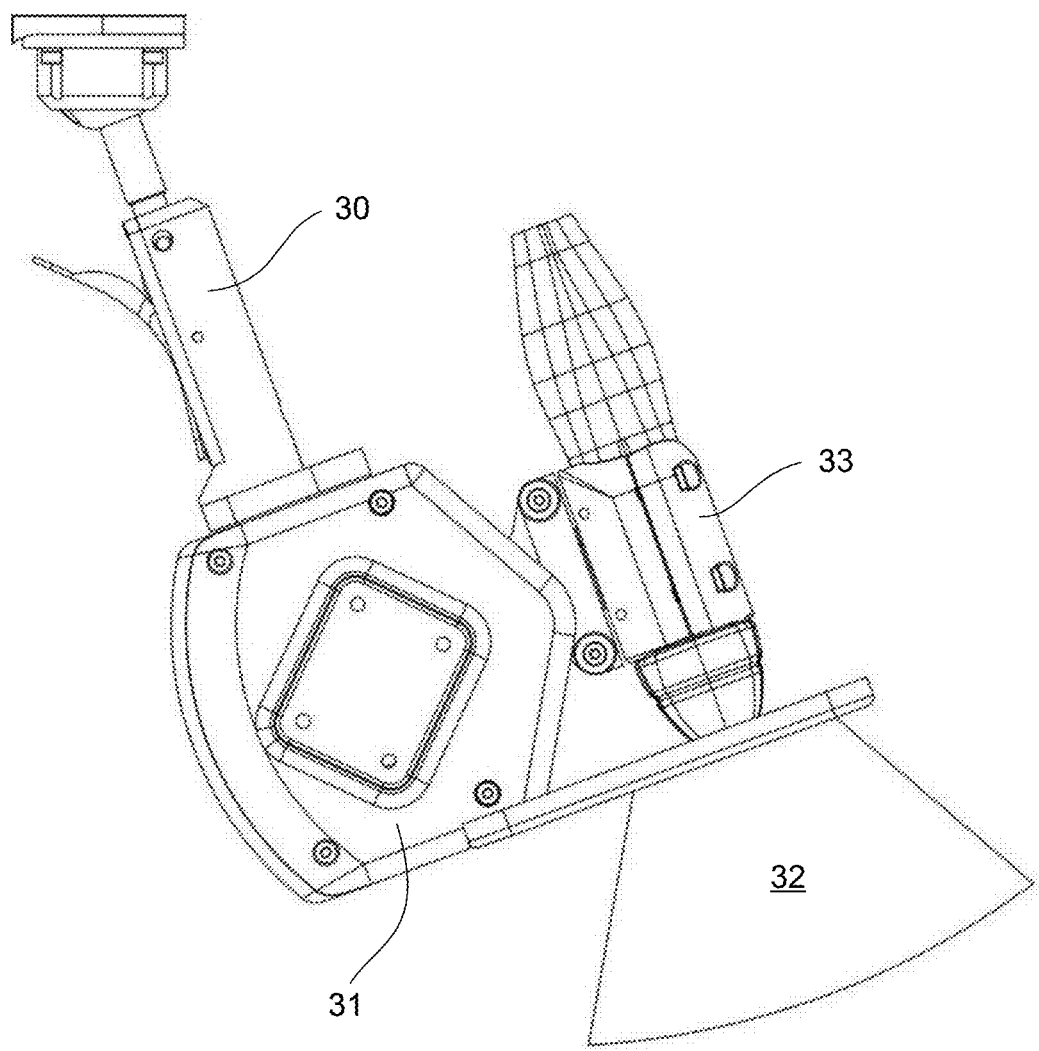
FIG. 2B depicts a magnified view of the ultrasound scanner depicted in FIG. 1B with the first embodiment of the locking mechanism linking the ultrasound scanner to the counterbalance apparatus.
Figure 2C:
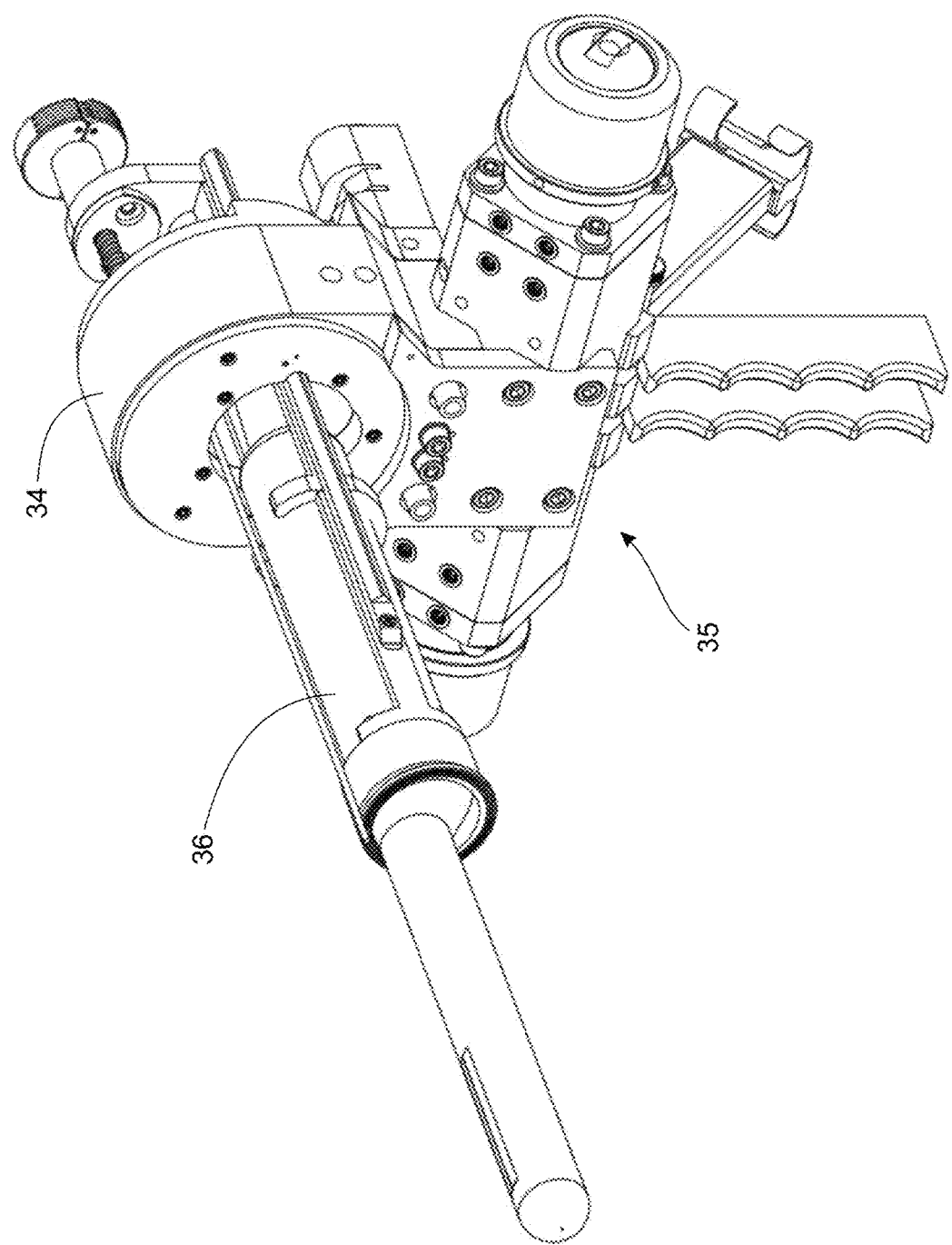
FIG. 2C depicts a central housing of the stabilizer assembly of FIG. 1C.
Figure 3A:
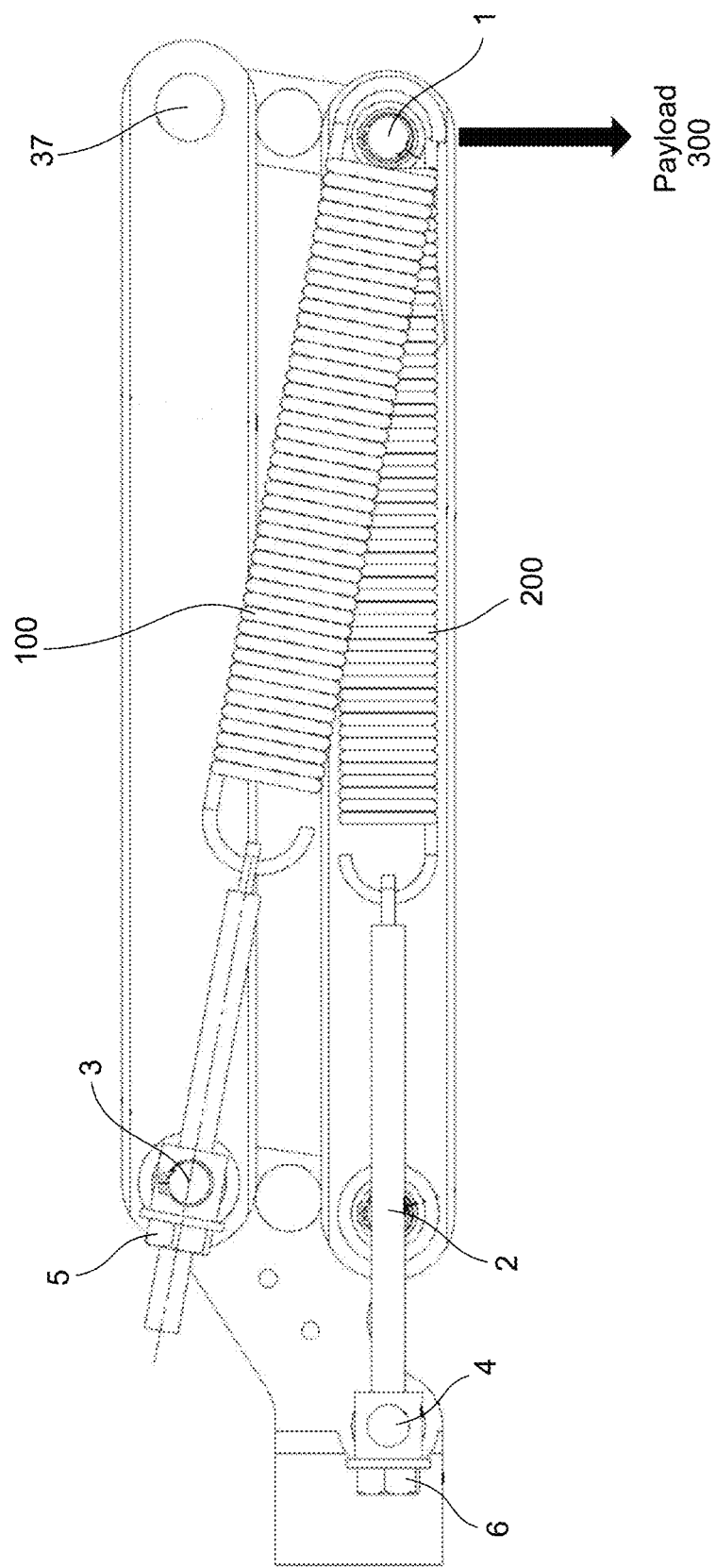
FIG. 3A depicts a second embodiment of a counterbalance apparatus integrated to support a payload attached to a pinned parallelogram.
Figure 3B:
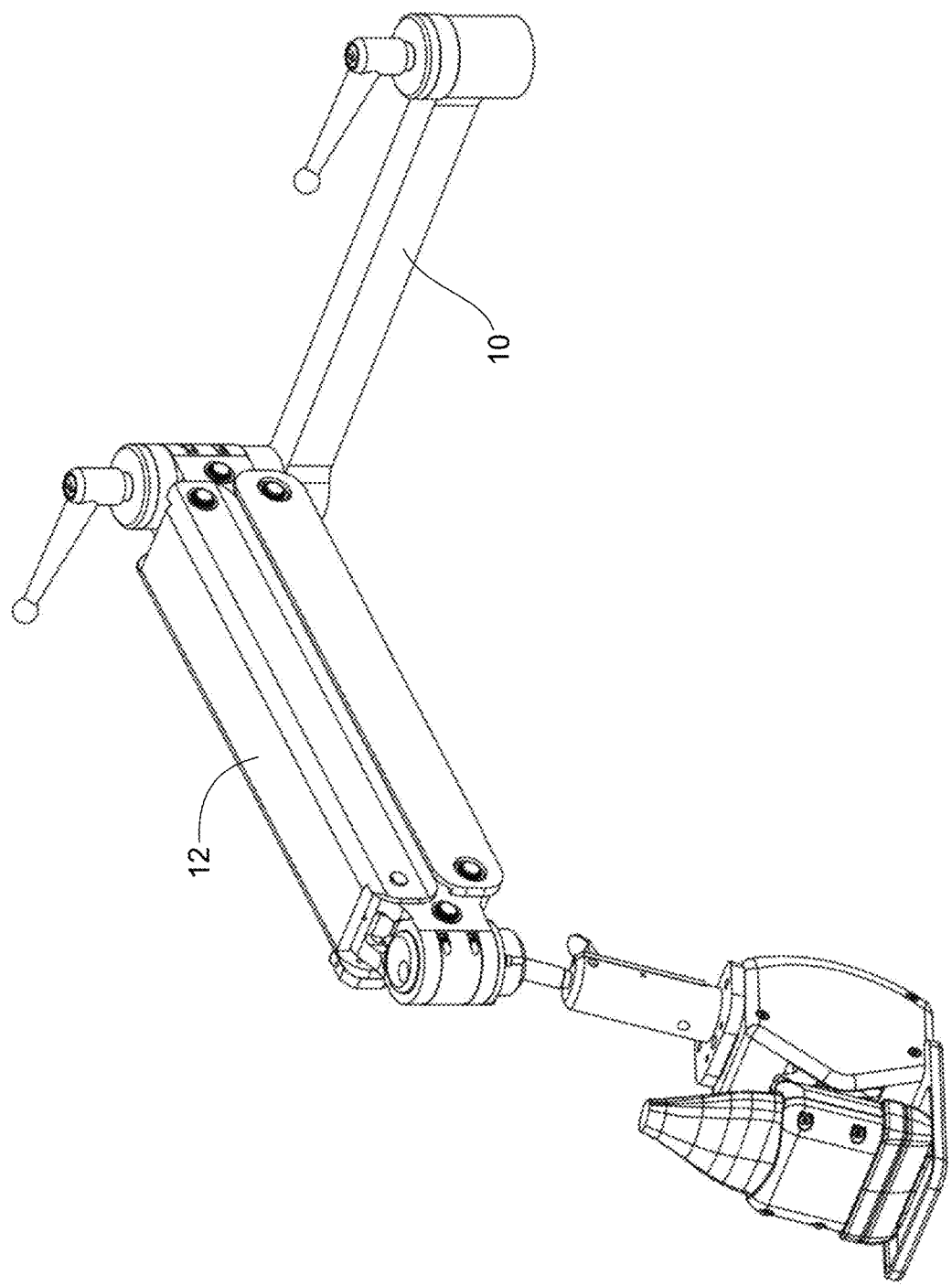
FIG. 3B illustrates another embodiment of a one-arm stabilizer assembly coupled to a counterbalance apparatus of FIG. 3A, the stabilizer supporting an ultrasound scanner linked to an end of the counterbalance apparatus.
Figure 3C:
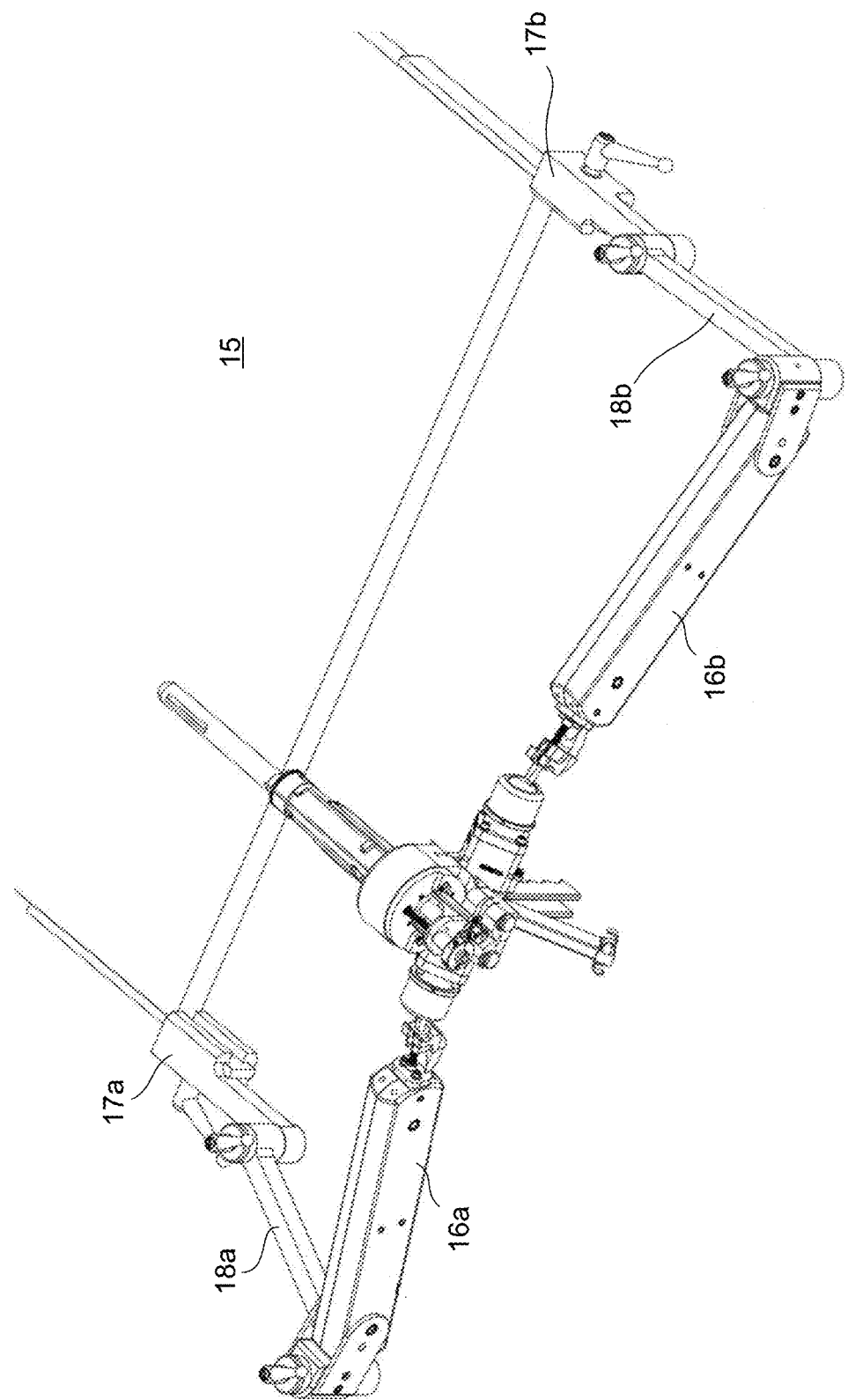
Figure 4A:
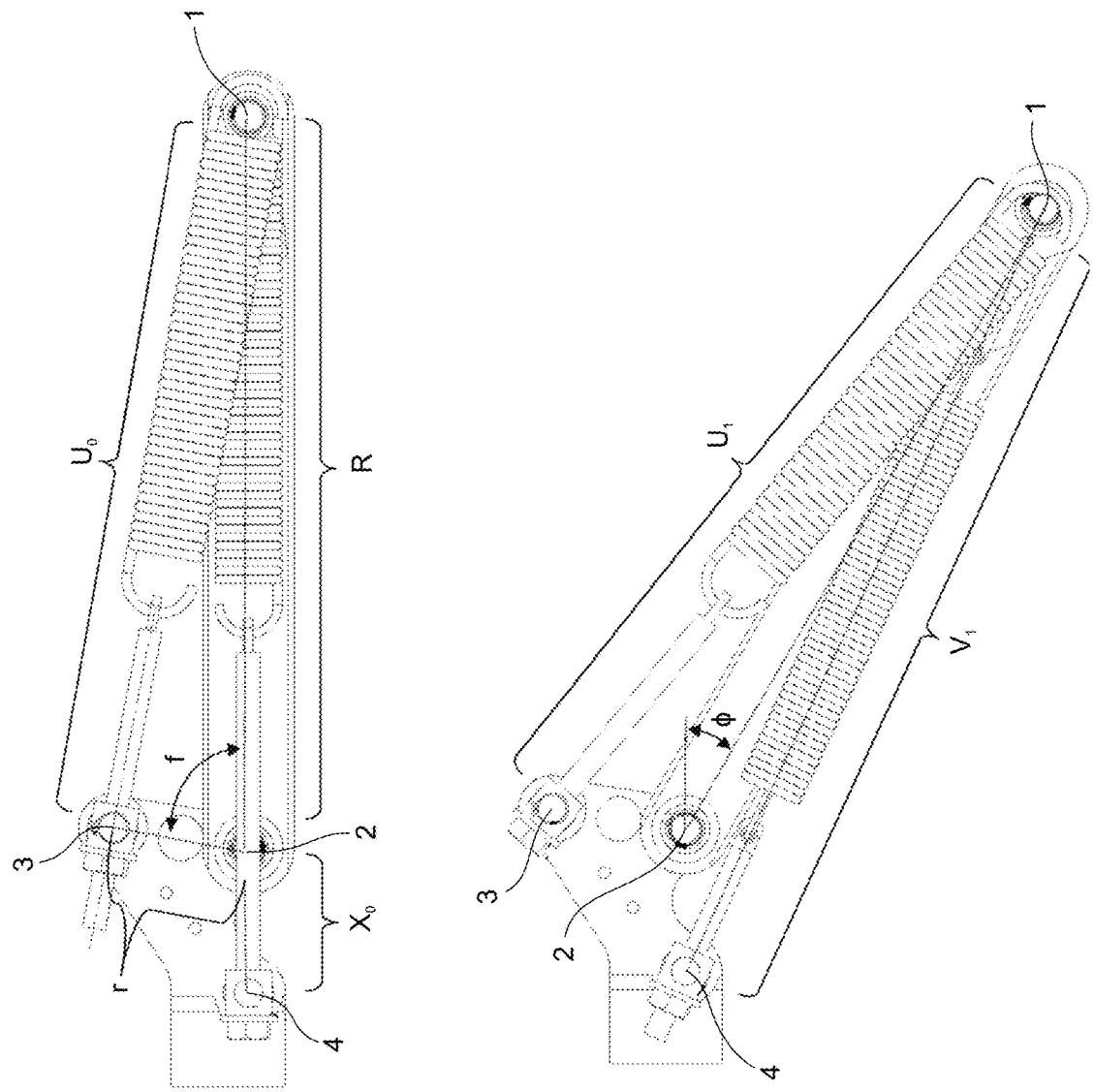
Figure 4B:
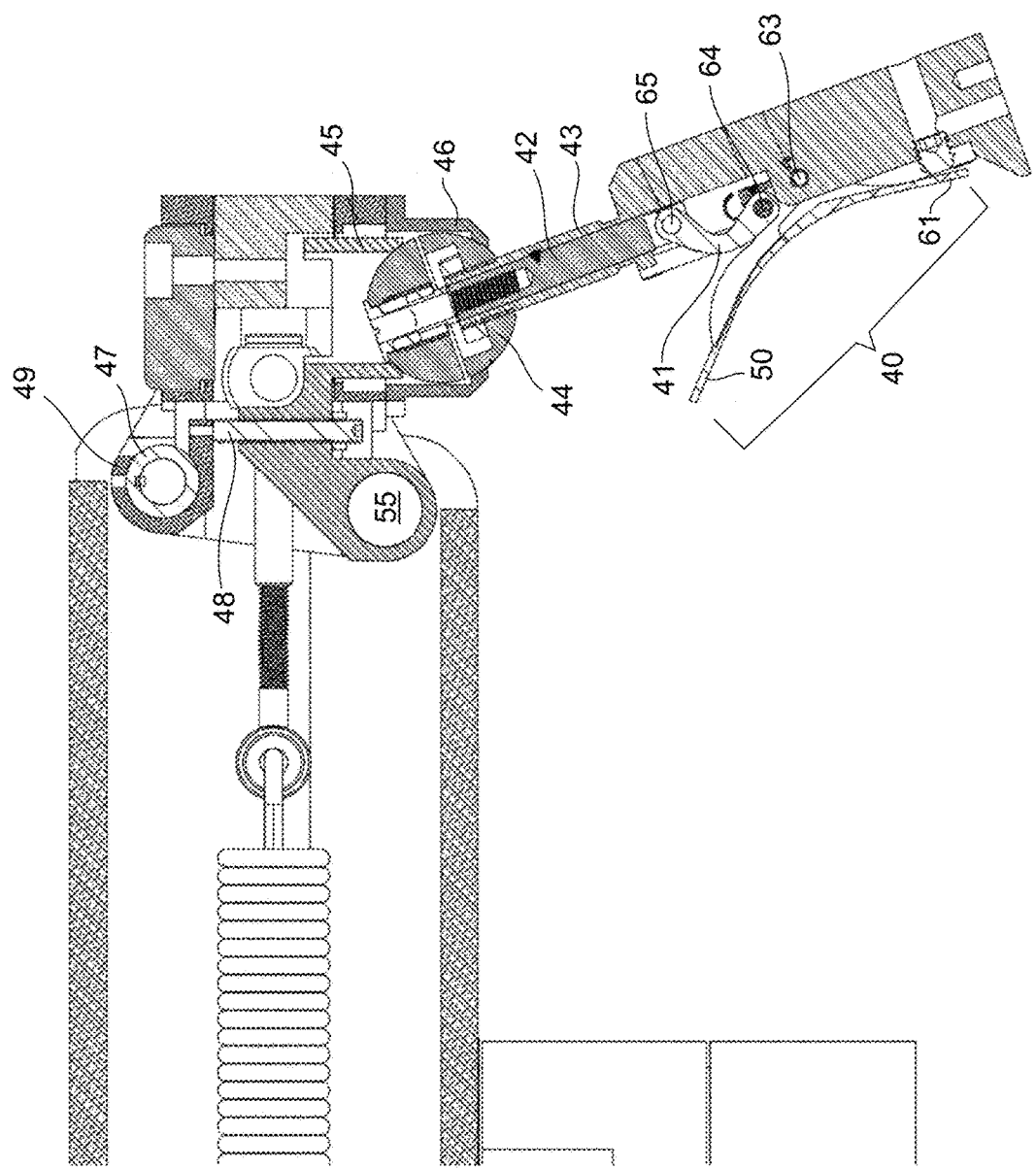
Figure 4C:
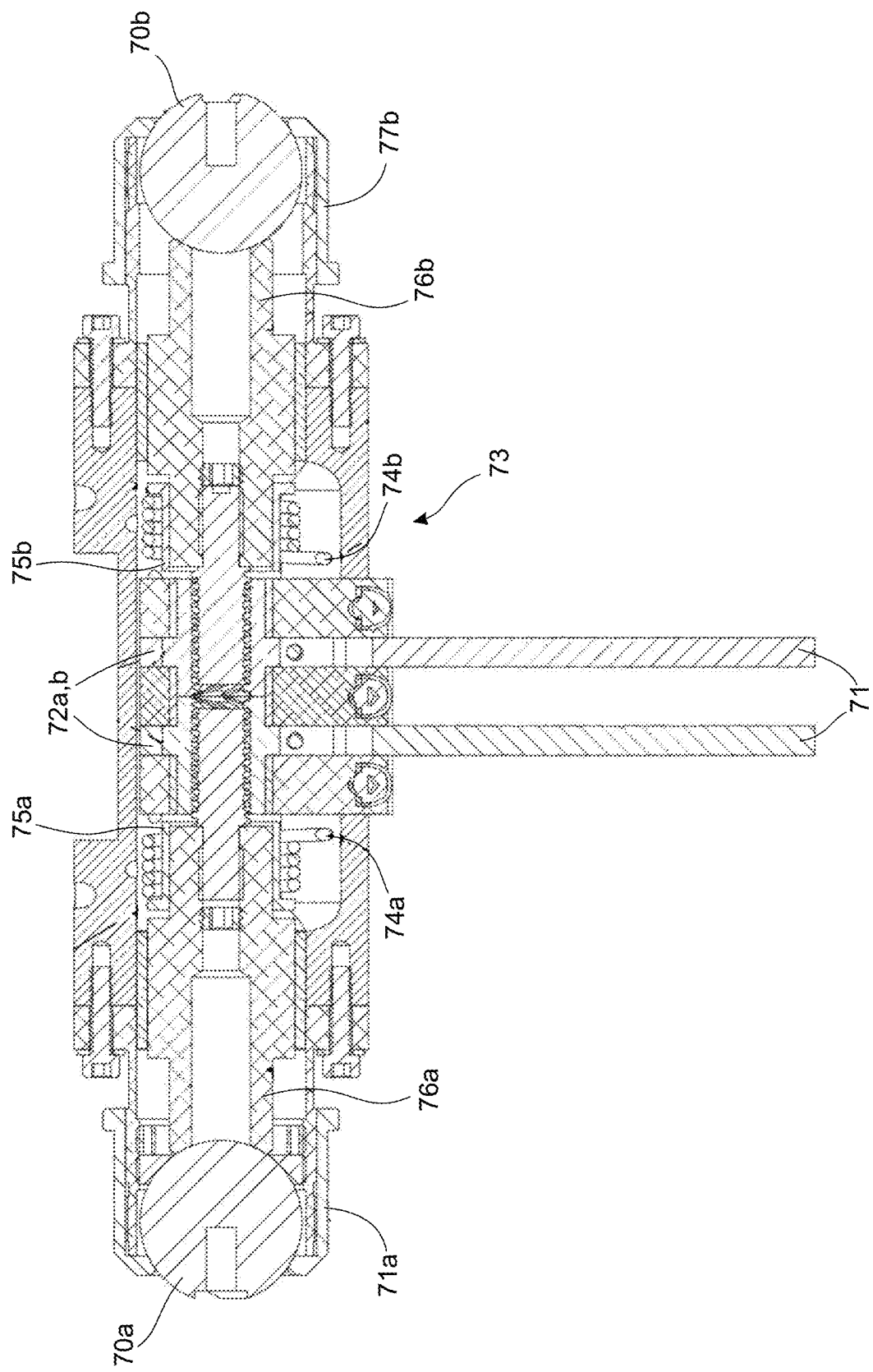
Figure 5A:
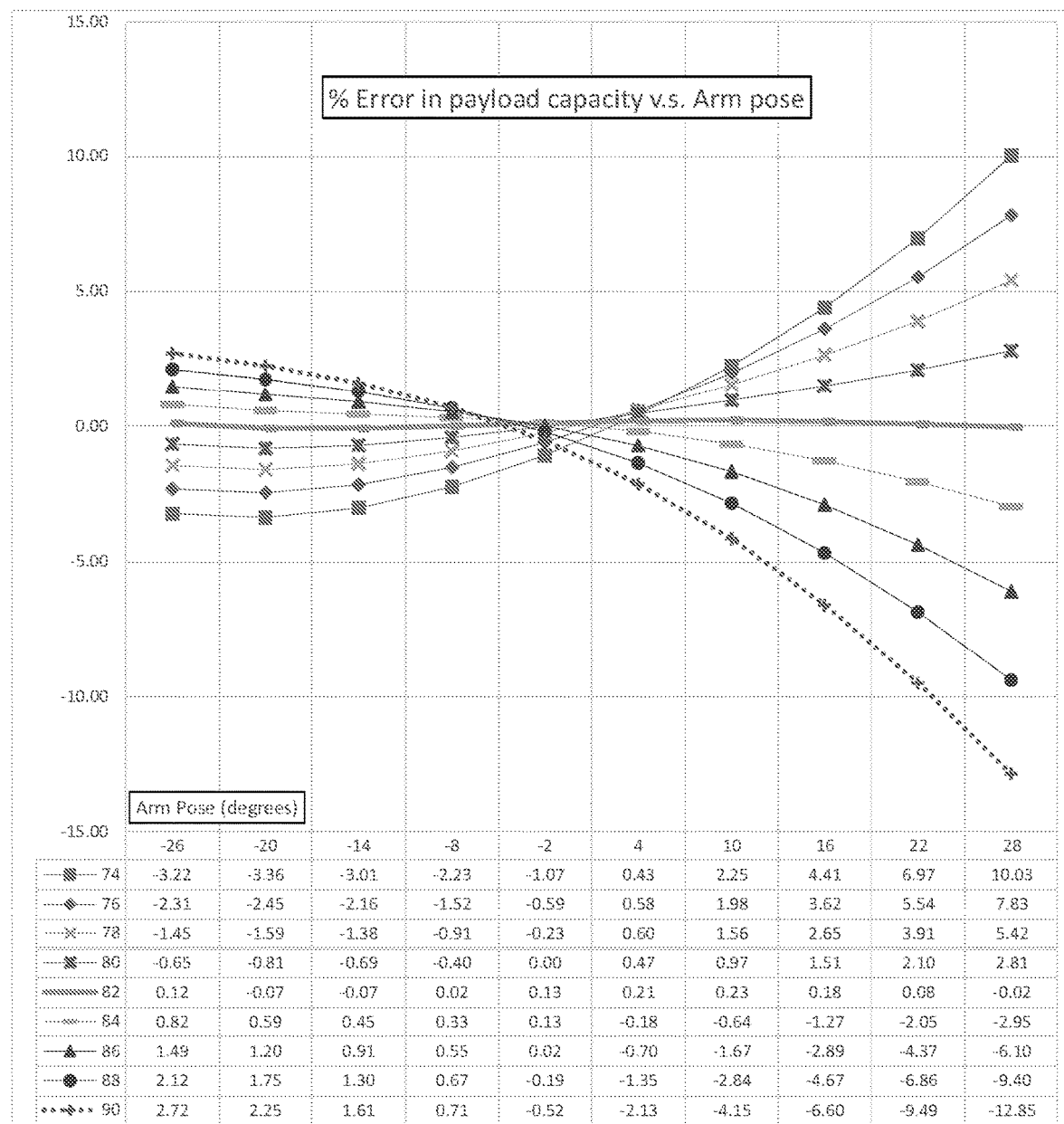
Figure 5B:
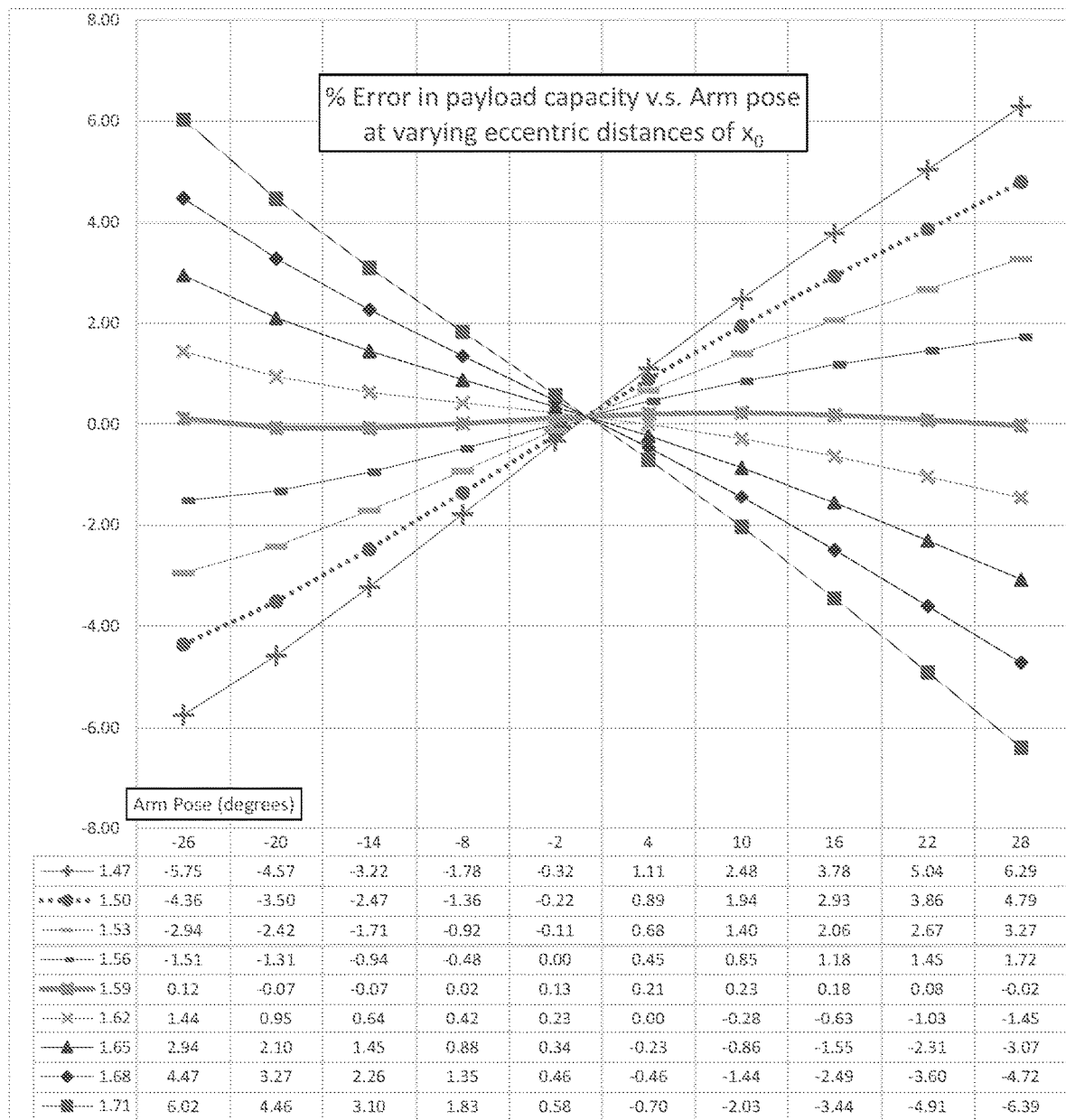

FIG. 3C depicts another embodiment of a two-arm stabilizer assembly, each arm comprising a counterbalance apparatus of the present invention, the stabilizer assembly supporting a medical device linked to ends of the counterbalance apparatuses, and the stabilizer assembly having the second embodiment of a locking mechanism for locking the medical device in place FIG. 4A depicts a free body diagram of an embodiment of the counterbalance system of FIG. 1A in equilibrium;

FIG. 4B depicts the locking mechanism of the stabilizer assembly of FIG. 2B in a section view in more detail;

FIG. 4C depicts a section view of a central head portion of the stabilizer assembly of FIG. 2C showing in detail the locking mechanism; and, FIG. 5A and FIG. 5B depicts graphs illustrating that a solution for unknown variables, a secondary resilient member offset $x_0$ (FIG. 5B), and an angle a primary resilient member makes with the horizontal $\varnothing$ (FIG. 5A), is different in a counterbalance of the present invention in comparison to the geometry for a commercially available extension spring (without the use of eccentric cams) which contain residual stresses that result in an initial tension in the spring.

DETAILED DESCRIPTION OF PREFERRED EMBODIMENTS

The description that follows, and the embodiments described therein, is provided by way of illustration of an example, or examples, of particular embodiments of the present invention. These examples are provided for the purposes of explanation, and not of limitation, of the invention. The drawings are not necessarily to scale and in some instances proportions may have been exaggerated in order to more clearly depict certain embodiments and features of the invention.

In this disclosure, a number of terms and abbreviations are used. The following definitions of such terms and abbreviations are provided. As used herein, a person skilled in the relevant art may generally understand the term "comprising" to generally mean the presence of the stated features, integers, steps, or components as referred to in the claims, but that it does not preclude the presence or addition of one or more other features, integers, steps, components or groups thereof.

In the description and drawings herein, and unless noted otherwise, the terms "vertical", "lateral" and "horizontal", are generally references to a Cartesian co-ordinate system in which the vertical direction generally extends in an "up and down" orientation from bottom to top (y-axis) while the lateral direction generally extends in a "left to right" or "side to side" orientation (x-axis). In addition, the horizontal direction extends in a "front to back" orientation and can extend in an orientation that may extend out from or into the page (z-axis). Unless indicated otherwise, the force or vector of gravity acts parallel to the y-axis (e.g., the vertical direction) in a general downward manner.

As used herein, a person skilled in the relevant art would understand that a parallelogram is a quadrilateral with two pairs of parallel sides. The opposite or facing sides of a parallelogram are of equal length and the opposite angles of a parallelogram are of equal measure. Parallelograms include, but are not limited to, rhomboids, rectangles, rhombuses, and squares. Those skilled in the relevant art would understand that a parallelogram of the present invention may be disposed in single or compound linkages, wherein it will be understood that a compound parallelogram generally may comprise two parallelograms with a common side.

As used herein, a person skilled in the relevant art would understand that a "resilient member" comprises one or more of any of the following elastic, pneumatic, gas spring, constant force spring motor, or other device adapted to store or exert mechanical energy, generate force and/or that is back-drivable (e.g., force applied to an output can move an input). In a preferred embodiment, a resilient member may comprise a spring-like device and in a more preferred embodiment, may comprise a compression or extension spring. While springs are represented in the Figures, persons skilled in the art will understand that any force generating device may be used in the system described herein.

As used herein, a person skilled in the relevant art will understand a "spring-like device" to refer to any device or structure that acts substantially like a compression or tension spring in providing resistance to a linear compression, expansion and/or tension along a longitudinal axis or resistance to bending which may produce a force at right angles to a long axis of the spring (e.g., a leaf or torsion spring). An example of a spring-like device is a unit of rubber or other resilient material or a pneumatic pressurized cylinder any one of which may be used in an equivalent manner to a compression or tension spring by providing resistance to a linear force along a longitudinal axis. Another example of a spring-like device is a spring, such as a compression spring or a tension spring. Compression springs are an example of a low-cost force generating device that are utilized to provide a simplified arrangement within the counterbalance assembly. A compression spring includes a longitudinal axis along which linear compressive forces are imposed as a result of rotational movement of a mechanical arm. Examples of compression springs include relatively standard die springs as commonly available in the industry. The exact number and size of such resilient members used in the counterbalance assembly described herein can vary depending upon the counterbalance torque desired, the size of the robotic arm involved, and the like, as will be recognized by the skilled person. There is a need in the art for apparatus and methods for exerting a force (e.g., to counteract the force of gravity) in order to reduce the physical effort exerted by users in various settings, including, but not limited to, medical professionals in performing medical examinations (e.g., ultrasound examinations). More particularly, there is a need in the art for an apparatus that can counterbalance a load for a user wherein the user can quickly and without additional effort pick up a payload with minimal effort.

An aspect of the present invention thereby preferably provides systems and methods to reduce the physical strain which may be experienced by users, including, but not limited to, medical practitioners who perform ultrasound examinations and similar medical procedures. It will be understood, however, that the present invention may be used to assist the performance of various tasks found in other settings, including, but not limited to, industrial environments.

A device and/or method according to the present invention is provided for resilient member aided counterbalancing and stabilization of a load.

(a) A Resilient Member Aided Counterbalancing Mechanism for a Shortened Arm or Linkage.

The present design facilitates the attachment of at least two resilient members to an arm or linkage preferably using a pin or hooked connection to support an attached load. Since the present invention comprises the integration of two or more resilient members (e.g., extension springs), it may be adapted for use with linkage systems that lack a counterbalancing mechanism. The present invention is simpler and more compact than other available prior art counterbalancing systems and facilitates simple adaptation to a linkage while preferably, but need not necessarily, adding a minimum amount of weight and/or inertia to the mechanism thus making it easier for the user to manipulate the payload. In addition, the present invention has the capacity to carry greater payloads than prior art designs. The present invention is an improvement on the counterbalance designs of the prior art, for example, Bax et. al. [1] where two orthogonal spring cam mechanical assemblies are replaced by two resilient members (e.g., extension springs) which are hooked to the base and distal end of the load carrying arm as illustrated in FIG. 1A.

An advantage of the invention using two resilient members that are extension springs compared to a pair of compression springs and abutted cams is the spring guides and cams in the original design are no longer required and therefore reduce the complexity and in turn reduce the mass and friction of the counterbalance apparatus making it easier for the user to manipulate the payload. The use of resilient members such as extension springs is not be desirable in prior art designs (e.g., Bax et. al. [1]) due to the pre-stress that are typically present in commercially available extension springs thus leading to a significant error in the counterbalancing system (see FIG. 2A). The use of resilient members, such as extension springs, that are stressed relieved can be used in place of the resilient member-cam pair using the geometry outlined in the design by Bax et al. [1] only if the ratio of the arm length (point "1" to point "2", FIG. 1A) to the primary spring offset (point "2" to point "4", FIG. 1A) is large. Persons skilled in the art understand that there is no fixed range for the ratio because the error in supporting the payload may depend on a number of factors. In addition to the ratio of the primary resilient member offset and arm length, the payload error are also dependent on how much error the user will tolerate, residual stresses in the relaxed resilient member, the resilient member stiffness K, and range of motion of the arm. Moreover, persons skilled in the art understand that extension springs are typically manufactured with an initial tension caused by the internal stresses created when the spring is wound. This internal stress holds the coils tightly together and an initial force may be required to initiate coil separation. Unlike a compression spring, which typically exerts zero load at zero deflection, an extension spring usually has a pre-load at zero deflection which is undesirable in many counterbalancing mechanisms.

Persons skilled in the art will understand that the effect of the resilient members in the present invention may be achieved by various approaches including but not limited to:

An extension spring.

A compression spring if member 100 is connected between points 37 and 2 in FIG. 3A and point 4 is positioned between points 2 and 1.

A urethane spring instead of the compression spring (above) if the apparatus is to be used in environments where ferrous components are not permitted (e.g., the bore of an MM).

A gas spring instead of an extension or a compression spring.

A leaf spring if the leaf springs are anchored at a fixed orientation at point 1 and the spring is abutted to points 3 and 4, which have an orientation that is phase shifted by 90 degrees about point 2 to the design that uses compression springs (above). The 90-degree phase shift is due to the leaf spring exerting its force at right angles to the long axis of the spring and the compression spring exerts its force parallel to the long axis of the spring. This design can also be used to counterbalance a payload in the bore of an MRI where ferrous materials used in compression and extension springs are not permitted.

An eccentrically loaded slender beam(s) (or curved beam) instead of one or two of the extension/compression springs of pinned to either 3-1 and 4-1 if the beam is in tension, or 37-2 and 4-1 where point 4 is between 2 and 1 if the beam is in compression. Similar to the leaf spring (above), this design may also be compatible for use in the bore of an MRI.

In addition to the foregoing, persons skilled in the art will understand that the resilient members do not have to be of the same type. For example, one member ("100") can be an extension spring and the other member ("200") can be a compression spring or any combination of the above examples.

Referring to FIG. 1A, a counterbalance apparatus includes a base (points "4", "2", and "3"), a load bearing arm (points "1" and "2") or linkage (see FIG. 3A), with a first and second resilient members ("100" and "200", respectively), and an adjustment mechanism ("5" and "6", respectively) for each member. The load bearing arm comprises at least one hinged link or a linkage comprising a plurality of pivot points forming one or more parallelogram linkages (see FIG. 3A), and in preferable embodiments projects from the base with at least one hinged connection and is adapted to support a payload at a distal end. The resilient member tension adjustment mechanism is pivotally connected to the base (3) and is adjustable between a load and a non-load bearing position by, for example, turning a nut. The counterbalance apparatus may use a toggle mechanism (not shown) in place of the nut as a means to pivot between the non-load bearing and the load bearing positions. The first resilient member is adapted to apply a force to the load bearing arm and comprises a first end connected to point (1) at the distal end of the arm and a second end connected to the adjustment member 5 located at pivot 3. The second resilient member is also adapted to apply a force to the load bearing arm and comprises a first end connected to point (1) at the distal end of the arm and a second end connected to a second adjustment point (4) at the base of the arm.

FIG. 1A is an illustration of an embodiment of the counterbalance apparatus integrated to support a payload attached to a hinged lever. The resilient members (e.g., extension springs; "100" and "200") are both hooked around the distal pinned connection (point "1") at one end such that the members can pivot freely around the shaft. Each resilient member is hooked around a bushing (or bearing) on the shaft (e.g., point "1") to allow each member to pivot freely and independently to each other. The opposite ends of each resilient member (arrows "100" and "200") are connected to adjustment nuts "5" and "6" which in turn are pinned to points (3) and (4) at the base of the arm in a location r (points "2" to "3") and $x_0$ (point "4" to "2") from the base pivot (point "2") and orientated at an angle Ø relative to the horizontal (angle formed by points "3", "2", "1") as shown In FIG. 4A.

FIG. 2A is a graph showing the percentage error in payload carrying capacity of an arm vs. arm pose relative to the horizontal in degrees for a resilient member balance design that uses two commercial extension springs in the design described by Bax et al. [1] in thin dotted line (i.e., lower line) and an improved design geometry outlined in this document (i.e., thick solid line or upper line). The use of resilient members that are extension springs is not be desirable in the prior art design [1] due to the pre-stress that may be present in commercially available extension springs in a shortened arm design where the ratio of the arm length to the primary spring offset is preferably 3.0/20. The design of the present invention reduces the counterbalancing error by about at least two orders of magnitude (thick solid line above in FIG. 2A) for an arm where the ratio of the arm length to the primary resilient member offset may be too large. Persons skilled in the art understand that there is no fixed range for the ratio because the error in supporting the payload depends on a number of factors. In addition to the ratio of the primary resilient member offset and arm length, the payload error is also dependent on how much error the user will tolerate, residual stresses in the relaxed resilient member, the resilient member stiffness K, and range of motion of the arm.

FIG. 3A is an illustration of an embodiment of the counterbalance apparatus integrated to support a payload attached to a pinned parallelogram (depicted by points "1", "2", "3", and "37").

The geometry of the resilient member placement (length $x_0$ and angle Ø) is determined by solving the equilibrium equation where the net torque due to gravity at the base of the arm must equal the sum of the anti-torques from each of the two (or more) resilient members; thus $$T_g = T_1 + T_2 \quad (1),$$

where $T_g$ is the torque about point 2 due to gravity and $T_1$ and $T_2$ are the respective anti-torque values from the resilient members 100 and 200. In terms of the arm geometry illustrated in FIG. 4A:

$$T_g = mg \cos \theta \quad (2),$$

$$T_1 = R\, k_1 \sin \beta_1 (\Delta x + u_1 - u_0) \quad (3),$$

$$u_1^2 = r^2 + R^2 - 2Rr \cos(\theta + \emptyset) \quad (3a),$$

$$u_0^2 = r^2 + R^2 - 2Rr \cos(\emptyset) \quad (3b),$$

$$T_2 = (x_0/v_1) k_2 R(R - v_1) \sin \theta \quad (4),$$

$$v_1^2 = x_0^2 + R^2 - 2Rx_0 \cos(\pi - \theta) \quad (4a),$$

FIG. 4A is a free body diagram of an embodiment of the resilient member aided counterbalance system in equilibrium. The variable $u_0$ represents the length of the primary member when the pose of the arm is horizontal (top) and at an arbitrary angle θ (bottom). The primary member is pre-stretched (including pre-stress that are present in the resilient member when it is unstretched) to counterbalance the load.

To minimize the net torque and its dependence on the pose of the arm, the objective function (∈) is minimized:

$$\in = \int_{\emptyset_1}^{\emptyset_2} M^2 d\emptyset \quad (5),$$

with respect to the variables that define the placement of the resilient members at the base of the arm. The critical points are preferably found by setting the partial derivatives of the objective function to zero and solving for the unknown variables: the secondary member offset $x_0$, and the angle the primary member makes with the horizontal Ø, thus:

$$\frac{\partial \in}{\partial x_0} = 0, \quad (5a)$$

$$\frac{\partial \in}{\partial \emptyset} = 0. \quad (5b)$$

The graphs in FIG. 5A and FIG. 5B illustrate a solution for the unknown variables: the secondary resilient member offset $x_0$, and the angle the primary resilient member makes with the horizontal Ø is different than the geometry outlined in Bax et al. for a commercially available extension spring (without the use of eccentric cams) which contain residual stresses that may result in an initial tension in the spring.

FIG. 5A and FIG. 5B illustrate the effect the variables that define the resilient member pose in FIG. 1A (% Error in payload capacity vs arm pose at varying eccentric distances of length $x_0$ (FIG. 5B) and % Error in payload capacity vs arm pose at varying angles of Ø (FIG. 5A)) has on the energy level of the objective function near to the critical points of equations 5a and 5b. For shortened arms like the example in FIG. 1A where the angle (depicted by points "3", "1" and "2") is larger than about 5 degrees, the error in the isoelasticity of the counterbalance is two orders of magnitude larger than the counterbalance geometry at the critical points $x_0$ and Ø. The dashed line in each graph represents the counterbalance error when the geometry described in [1] is used.

(b) Application of the Counterbalance Apparatus: A One Arm Stabilizer Assembly for the Precise Control and Fixation of the Position and Orientation of a Medical Device.

The single arm stabilizer assembly comprises a trigger activated locking mechanism coupled to a counterbalancing linkage by, for example, a ball joint located at the distal end of the counterbalance arm. The counterbalancing linkage comprises at least two links pivotally connected to each other facilitating both vertical and horizontal movement of the linkage. When connected to the locking mechanism, the counterbalancing assembly facilitates the motion of the payload with six degrees of freedom and preferably fully supports the mass of the attached payload with at least three degrees of freedom.

Figure 1B:
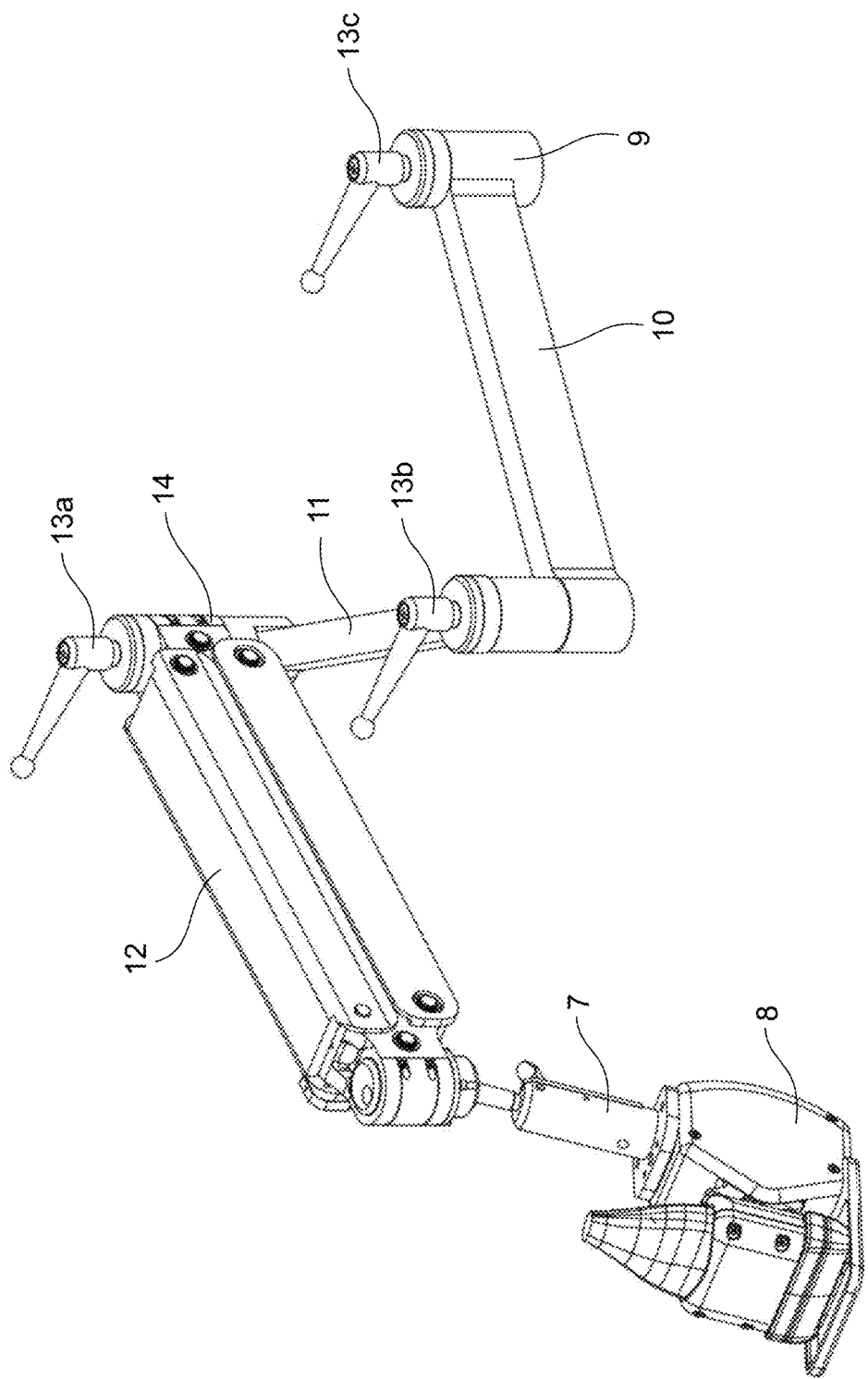
FIG. 1B depicts an embodiment of a one-arm stabilizer assembly comprising a counterbalance apparatus of the present invention, the stabilizer assembly supporting an ultrasound scanner linked to an end of the counterbalance apparatus, and the stabilizer assembly having a first embodiment of a locking mechanism for locking the ultrasound scanner in place.

FIG. 1B shows an embodiment of the stabilizer assembly which may be mounted onto an operating room bed (e.g., where a patient may be positioned) or table and optionally supporting a medical device (e.g., a 3D ultrasound scanner for breast imaging). In one embodiment, the stabilizer assembly may also be mounted on a floor, ceiling, cart or another grounded fixture (e.g., an ultrasound machine). The embodiment of the stabilizer assembly shown is supporting a 3D ultrasound scanner (FIG. 2B, elements "7" and "8") and holding a 2D ultrasound probe (FIG. 2B, element 33) located at a distal end of the stabilizer assembly. The ultrasound probe and scanner shown in FIG. 1B may preferably be used for breast imaging and illustrates one of many possible uses of the stabilizer assembly.

At a base end of the stabilizer (FIG. 1B, element "9"), a first link (FIG. 1B, element "10") is pivotally connected (e.g., a vertical hinged connection) to facilitate free rotation of the attached link in a horizontal plane. As shown in FIG.

1B, an additional link (FIG. 1B, element "11") is pivotally attached to a distal end of the first link (e.g., a vertically orientated hinged connection) to provide, for example, a total of two degrees of motion in a horizontal plane. Connected to the second link is the counterbalancing arm (FIG. 1B, element "12") by, for example, a universal joint (FIG. 1B, element "14"), which facilitates pivotal movement of the counterbalance arm both in the horizontal and vertical planes. Together, the three connected links facilitate the manipulation of a payload using the counterbalance assembly in a total of three degrees of freedom.

At each hinged connection in the counterbalance assembly, there is a locking element (FIG. 1B, elements "13a, 13b, 13c") which may be adapted to lock the relative rotation of each link when a threaded handle is tightened, forcing each link together forming a friction connection. The locking mechanism used in this design is preferably a conventional design used to lock rotary joints and is not described in further detail here.

FIG. 2B illustrates the locking mechanism (element "30") and attached ultrasound scanner (element "31") mounted on a bottom. The locking mechanism contains a trigger activated toggle linkage within to lock the height and orientation of the attached scanner. The scanner illustrated in FIG. 2B is a two degree of freedom motorized unit that may be used to collect two-dimensional ultrasound images and reconstruct these two-dimensional images into a three-dimensional image (element "32") for analysis and guidance of a therapy needle for, for example, brachytherapy.

The counterbalance linkage illustrated in FIG. 1B, is one of many possible combinations of connected links that accomplish the same flexibility where a minimum of one horizontal and one vertical link is needed to provide the same flexibility as in FIG. 1B. FIG. 3B illustrates an alternate embodiment which contains one horizontal (FIG. 3B, element "10") and vertical linkage (FIG. 3B, element "12") in the stabilizer assembly. The additional horizontal link in FIG. 1B increases the range of motion of the stabilizer, but still provides three degrees of freedom. When connected to a payload (e.g., locking mechanism and 3D ultrasound scanner) using a ball joint, for example, the total flexibility of the stabilizer becomes six degrees of freedom (i.e., three degrees of linear and angular motion).

FIG. 3B illustrates the stabilizer assembly in its preferred embodiment where a minimum of two links may be used in the counterbalance assembly: one link to facilitate motion in a horizontal plane and one arm to facilitate motion in a vertical plane.

FIG. 4B shows an embodiment of the locking mechanism of the stabilizer assembly in a section view in more detail. The locking mechanism in FIG. 4B comprises a handle which is part of a toggle linkage (FIG. 4B, elements "40"-"41") that may be connected (e.g., pinned) to a locking shaft (FIG. 4B, element "42") that is slidably mounted to the main body of the locking mechanism. The locking shaft extends vertically (e.g., upward) through a bushing in the main body (FIG. 4B, element "43") to a split ball joint (FIG. 4B, element "44"). The shaft is rigidly attached to an upper half of the split ball joint while the lower half of the ball is rigidly attached to a main body (FIG. 4B, element "43") of the trigger mechanism. To lock the arm in position, the user would press an upper lever (FIG. 4B, element "60") until the toggle linkage is in a locked position (when pivot points depicted by elements "63", "64" and "65" are approximately in line). This forces the split ball to spread open which in turn may force the assembly to be wedged between the upper (FIG. 4B, element "45") and the lower (FIG. 4B, element "46") socket assembly that contains the ball joint. The lower socket containing the ball joint is rigidly attached to the counterbalancing arm while the upper socket containment nut (FIG. 4B, element "45") is pivotally connected to a hinged connection (FIG. 4B, element "55") on the counterbalancing arm and in turn engages a brake pad (FIG. 4B, element "49"). When the ball is in the locked position, a setscrew (FIG. 4B, element "48") on arm (FIG. 4B, element "45") pushes up against the brake pad and in turn locks the position of the brake drum (FIG. 4B, element "47") at hinged points (FIG. 4B, elements "55" and "47"). Therefore, when the ball becomes locked, the vertical movement of the arm also becomes locked at the same time. To release the ball joint and arm height, the user would squeeze the lower trigger (FIG. 4B, element "61") and the split ball joint closes allowing the attached scanner to move freely.

(c) Application of the Counterbalance Apparatus: A Two Arm Stabilizer Assembly for the Precise Control and Fixation of the Position and Orientation of a Medical Device.

The stabilizer assembly comprises a central housing containing a trigger activated locking mechanism which in turn is coupled to two counterbalancing assemblies by, for example, a pair of ball joints located at each end of the central housing. Each counterbalancing linkage comprises at least two links pivotally connected to each other allowing both vertical and horizontal movement of the linkage. When connected to the central housing, the two counterbalancing mechanisms facilitate motion of and fully supports the mass of a payload with six degrees of freedom.

Figure 1C:
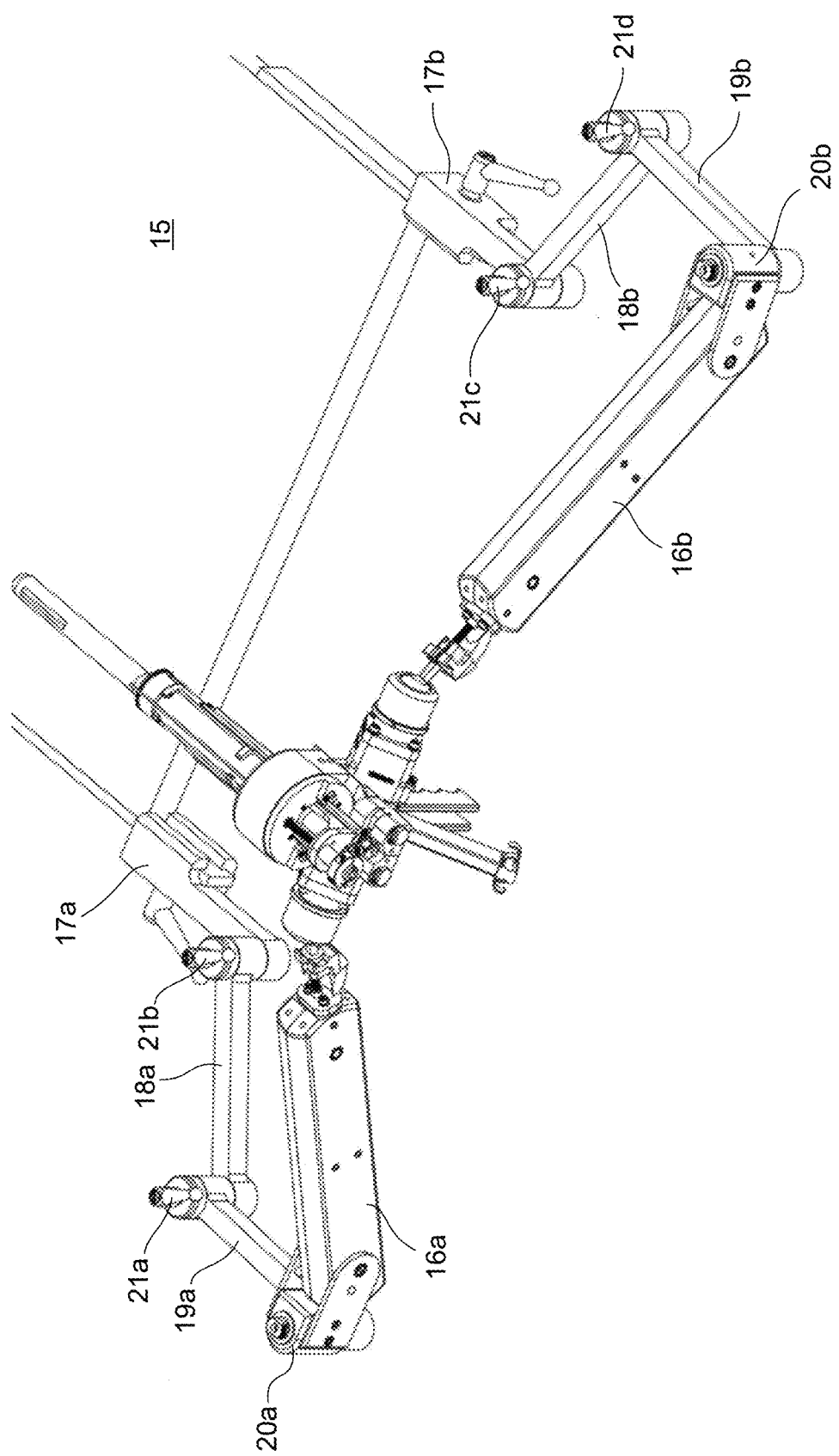
FIG. 1C depicts the two-arm stabilizer assembly, each arm comprising a counterbalance apparatus of the present invention, the stabilizer assembly supporting a medical device linked to ends of the counterbalance apparatuses, and the stabilizer assembly having a second embodiment of a locking mechanism for locking the medical device in place.

FIG. 1C shows an embodiment of the stabilizer assembly, supporting a medical device (e.g., a stepper and ultrasound imaging probe) for brachytherapy, mounted onto an operating room bed (FIG. 1C, element "15") where a patient may be positioned. The stabilizer assembly can also be mounted on a floor, ceiling, cart or another grounded fixture (e.g., an ultrasound machine). The stepper assembly shown supports a stepper apparatus and attached ultrasound probe for fine positioning of the probe about a roll axis and longitudinal direction of the ultrasound probe (FIG. 2C). The embodiment of the ultrasound probe and stepper shown in FIG. 1C is used for brachytherapy and illustrates one of many possible uses of the stabilizer assembly. The stepper apparatus and its use for brachytherapy is not described in detail but is only intended to illustrate how the stabilizer can be used.

FIG. 2C is an illustration of an embodiment of the central housing and stepper/scanner assembly (34) mounted on top. The central housing (35) comprises a trigger activated locking mechanism within to lock the height and orientation of the attached stepper/scanner. The embodiment of the stepper/scanner illustrated is a two degree of freedom motorized unit that is used, for example, to collect 2D ultrasound images with the attached probe (36) and reconstruct them into a 3D image for analysis and guidance of a therapy needle for brachytherapy.

An embodiment of the stabilizer assembly comprises two identical counterbalancing linkages attached to either end of the central housing. The central housing (FIG. 2C, element "35") preferably contains a trigger activated locking mechanism and also is where the payload is attached: stepper (FIG. 2C, element "34") and ultrasound probe (FIG. 2C, element "36") in FIG. 1C. Both the left (FIG. 1C, element "16a") and right side (FIG. 1C, element "16b") counterbalancing linkage are identical and each assembly comprises a mounting clamp (FIG. 1C, element "17a, 17b") at a base to allow the stabilizer to be attached securely to, for example, an operating room bed (FIG. 1C, item "15") or other grounded fixture. At a distal end of the mounting clamp a first link is connected by means of a vertical hinged connection to allow the attached link to rotate freely in a horizontal plane. An additional link (FIG. 1C, element "19a, 19b") is attached to the distal end of the first link (FIG. 1C, element "18a, 18b") by means of a vertically orientated hinged connection to give a total of two degrees of motion in the horizontal plane. In one embodiment, connected to the second link is the counterbalancing arm (FIG. 1C, element "16a, 16b") by means of for example a universal joint (FIG. 1C, element "20a, 20b"), which facilitates pivoting of the counterbalance arm in both the horizontal and vertical planes.

Together, the three connected links facilitate the counterbalance assembly to manipulate a payload a total of three degrees of freedom. The counterbalancing mechanism is disclosed in detail, in section (a) "A counterbalancing mechanism for a shortened arm or linkage" above. At each hinged connection in the counterbalance assembly, there is a locking element (FIG. 1C, element "21a, 21b, 21c, 21d") which locks the relative rotation of each link when the threaded handle is tightened, forcing each link together forming a friction connection. The locking mechanism used in this design is a conventional design used to lock rotary joints and is not described in further detail here.

The counterbalance linkage illustrated in FIG. 1C, is one of many possible combinations of connected links that will accomplish the same flexibility where a minimum of one horizontal and one vertical link is needed to provide the same flexibility as in FIG. 1C. FIG. 3C illustrates an alternate embodiment (preferred) which contains one horizontal (FIG. 3C, element "18a, 18b") and vertical link (FIG. 3C, element "16a, 16b") in the stabilizer assembly. The additional horizontal link in FIG. 1C (FIG. 1C, element "19a, 19b") increases the range of motion of the stabilizer, but still provides three degrees of freedom. When connected to the central housing by means of, for example, two ball joints, the total flexibility of the stabilizer increases to six degrees of freedom (i.e., three degrees of linear and angular motion).

FIG. 3C illustrates the stabilizer assembly in its preferred embodiment where a minimum of two links are required for each counterbalance assembly: one link (element "18a, 18b") to facilitate motion in the horizontal plane and one arm (element "16a, 16b") to facilitate motion in the vertical plane. Together, both counterbalance assemblies give the attached payload a total of six degrees of freedom.

FIG. 4C is a section view of the central head portion of the stabilizer assembly showing in detail the stabilizer locking mechanism. The brake shoe is pressed up against the ball joint by means of a male thread on the brake shoe body that engages with a matching nut to which the spring-loaded trigger is attached. To release the ball joints, the user would squeeze the trigger, and the threaded nuts would then force the brake shoe(s) away from the balls, allowing the ball joints to pivot freely.

FIG. 4C shows the central head portion of an embodiment of the stabilizer assembly in a section view to show more detail of how the locking mechanism works. The locking mechanism comprises two identical sub-assemblies, each one responsible for locking the left (FIG. 4C, element "70a") and right ball (FIG. 4C, element "70b") respectively. The locking mechanism comprises a handle (FIG. 4C, element "71") fixed to a threaded nut (FIG. 4C, element "72a, 72b") which extends downward from the central housing (FIG. 4C, element "73"), a resilient member (e.g., torsion spring; FIG. 4C, element "74a, 74b") supported by a floating mandrel (FIG. 4C, element "75a, 75b"), and a threaded brake shoe (FIG. 4C, element "76a, 76b") that is received by a threaded nut (FIG. 4C, element "72a, 72b"). Each ball is locked into place by a brake shoe (FIG. 4C, element "76a, 76b") that is pressed up against the ball forcing it up against the lip of the captive nut (FIG. 4C, element "77a, 77b"). The trigger is resilient member aided (e.g., a torsion spring) that causes the nut to push up against the ball locking it in place. To release the ball joints, the user would squeeze the trigger and the threaded nuts would then force the brake shoe(s) away from the balls, allowing the ball joints to pivot freely.

Other modifications and alterations may be used in the design and manufacture of other embodiments according to the present invention without departing from the scope of the invention, which is limited only be the claims.

The invention claimed is:

1. A counterbalance apparatus for supporting a load having a load vector applied in a direction of the vector of gravity, comprising:
    a base;
    a load bearing arm comprising a plurality of pivot points forming one or more parallelogram linkages projecting from the base at an attachment point at a proximal end and adapted to support the load at a distal end;
    a first resilient member for applying a force to the load bearing arm having a first end connected to a position at the distal end of the arm and a second end connected to a first adjustment member pivotally connected to the base and positioned at a first proximal end of the arm;
    a second resilient member for applying a force to the load bearing arm having a first end connected to a same position as the first resilient member at the distal end of the arm and a second end connected to a second adjustment member pivotally connected to the base and positioned at a second proximal end of the arm;
    the first and second adjustment members moveable between a non-load bearing and a load bearing position; and
    wherein movement of the first and/or second adjustment members from the non-load bearing position to the load bearing position engages the forces of the first and second resilient members to counterbalance the load vector.

2. The counterbalance apparatus of claim 1 wherein the resilient members are extension springs.

3. The counterbalance apparatus of claim 1 further adapted to support a load attached to a pinned parallelogram.

4. The counterbalance apparatus of claim 1 pivotally coupled to a single arm stabilizer, the single arm stabilizer further comprising a trigger activated locking mechanism to prevent movement of the single arm stabilizer.

5. The counterbalance apparatus of claim 1 pivotally coupled in a two-armed stabilizer.

6. A method of supporting a load having a load vector applied in a direction of the vector of gravity using a counterbalance apparatus, the method comprising:
    attaching the load to a distal end of a load bearing arm projecting from a base at an attachment point at a proximal end, the load bearing arm with a plurality of pivot points forming one or more parallelogram linkages;
    configuring a first resilient member to apply a force to the load bearing arm by connecting a first end to a position at the distal end of the arm and a second end to a first adjustment member pivotally connected to the base and positioned at a first proximal end of the arm;

configuring a second resilient member to apply a force to the load bearing arm by connecting a first end to a same position as the first resilient member at the distal end of the arm and a second end to a second adjustment member pivotally connected to the base and positioned at a second proximal end of the arm;

adjusting the first and second adjustment members between a non-load bearing and a load bearing position; and whereby moving the first and/or second adjustment members from the non-load bearing position to the load bearing position engages the forces of the first and second resilient members to counterbalance the load vector.

7. The method of claim 6 wherein the resilient members are extension springs.

\* \* \* \* \*